United States Patent
Ranganathan et al.

(10) Patent No.: US 6,706,287 B2
(45) Date of Patent: Mar. 16, 2004

(54) PREBIOTIC AND PROBIOTIC COMPOSITIONS AND METHODS FOR THEIR USE IN GUT-BASED THERAPIES

(75) Inventors: Nataragan Ranganathan, Broomall, PA (US); Jack Dickstein, Huntingdon Valley, PA (US); Raj Mehta, King of Prussia, PA (US)

(73) Assignee: Kibow Biotech Inc., Philadelphia, PA (US)

( * ) Notice: Subject to any disclaimer, the term of this patent is extended or adjusted under 35 U.S.C. 154(b) by 249 days.

(21) Appl. No.: 09/855,346

(22) Filed: May 15, 2001

(65) Prior Publication Data

US 2002/0187134 A1 Dec. 12, 2002

(51) Int. Cl.[7] ................................. A61K 9/50
(52) U.S. Cl. ................. 424/490; 424/725; 424/780; 424/234.1
(58) Field of Search ................. 424/725, 735, 424/780, 490, 496, 500, 234.1, 246.1

(56) References Cited

U.S. PATENT DOCUMENTS

| | | | |
|---|---|---|---|
| 4,581,141 A | * 4/1986 | Ash | |
| 5,032,399 A | 7/1991 | Gorbach et al. | ............... 424/93 |
| 5,531,988 A | 7/1996 | Paul | ............... 424/93.4 |
| 5,698,190 A | * 12/1997 | Hider et al. | |
| 5,733,568 A | 3/1998 | Ford | ............... 424/433 |
| 5,840,318 A | 11/1998 | Marshall et al. | ........ 424/282.1 |
| 5,968,569 A | * 10/1999 | Cavadini et al. | |
| 6,180,099 B1 | * 1/2001 | Paul | |

FOREIGN PATENT DOCUMENTS

| | | | |
|---|---|---|---|
| JP | 59110621 A | * | 6/1984 |
| WO | WO 97/26903 | * | 7/1997 |

OTHER PUBLICATIONS

Giovannetti et al., "Oral activated Charcoal in Patients with Uremic Pruritus", Nephron, 1995, 70 (2):193–6.*

Asher et al., "Projections and measurements of in vivo performance of liquid membrane capsules", Kidney Int. 1976 10:S–254–S–258.

Bezkorovainy A., "Probiotics:determinants of survival and growth in the gut [1-3]", Am. J. Clin. Nutr. 2001 73 (Suppl): 399S–405S.

Bliss et al., "Supplementation with gum arabic fiber increases fecal nitrogen excretion and lowers serum urea nitrogen concentration in chronic renal failure patients consuming a low–protein diet [1-4]", Am. J. Clin. Nutr. 1996 63:392–398.

Chang, T.M.S. (Artificial Cells, Chapter 5, in Biomedical Applications of Microencapsulation, edited by Lim, F. CRC Press Florida, pp 86–100.

Chang T.M.S., "Assessments of clinical trials of charcoal hemoperfusion in uremic patients", Clin. Neph. 1979 11:111–119.

Clark et al., Perfusion of Isolated Intestinal Loops in the Management of Chronic Renal Failure, Trans. Am. Soc. Artif. Intrn. Organs 1962 8:246–251.

Cummings J.H. et al., Prebiotic digestion and fermentation [1-3], Am. J. Clin. Nutr. 2001 73 (Suppl): 415S–420S.

Dunn et al., "Gas Chromatographic Determination of Free Mono–, Di–, and Trimethylamines in Biological Fluids", Analytical Chemistry 1976 48:41–44.

Einbacher and Carter, "The Role of the Microbial Flora in uremia", J. Exp. Med. 1966 123:239–250.

Friedman et al., "Hypertrigylceridemia Responsive to Charcoal Sorption", Proc. Clin. Dia. Trans. Forum 1977 7:183–184.

Giordano et al., "Further studies with oxystarch", Kidney Int. 1976 10:S–266–S–268.

Goldenhersh et al., "Effect of microencapsulation on competitive adsorption in intestinal fluids", Kidney Int. 1976 10:S–251–S–253.

Gotch et al., "Theoretical Considerations on Molecular Transport in Dialysis and Sorbent Therapy for Uremia", Journal of Dialysis 1976–1977 1(2) :105–144.

Jenkins D.J. et al., "Inulin, Oligofructose and Intestinal Function[1]", J. Nutr. 1999 129: 1431S–1433S.

Kjellstrand et al., "On the Clinical use of Microencapsulated Zirconium Phosphate–Urease for the Treatment of Chronic Uremia", Trans. Am. Soc. Artif. Intern. Organs 1981 27:24–29.

Koliff, W.J., "Longitudinal perspectives on sorbents in uremia", Kidney Int. 1976 10:S–211–S–214.

Miyazaki T. et al., "An oral sorbent reduces overload of indoxyl sulphate and gene expression of TGF–$\beta$1 in uraemic rat kidneys", Nephrol Dial Transplant 2000 15: 1773–1781.

Nagano et al., "Pharmacological properties of chitosan–coated dialdehyde cellulose (chitosan DAC), a newly developed oral adsorbent (II). Effect of chitosan DAC on rats with chronic renal failure induced by adriamycin", Medline Abstract UI 96058336 1995.

Okada, K. and Takahashi, S., "Correction by oral adsorbent of abnormal digestive tract milieu in rats with chronic renal failure", Nephrol. Dial. Transplant. 1995 10:671–676.

(List continued on next page.)

Primary Examiner—Leon B. Lankford, Jr.
Assistant Examiner—Ruth A. Davis
(74) Attorney, Agent, or Firm—Licata & Tyrrell P.C.

(57) ABSTRACT

Microencapsulated and/or enteric coated compositions containing a mixture of probiotics, prebiotics and ammoniaphilic bacteria with high urease activity with or without sorbents with specific adsorption affinities for uremic toxins such as creatinine, uric acid, phenols, indoles, middle molecular weight molecules and inorganic phosphate and water absorbents are provided. Also provided are methods of alleviating symptoms of uremia in a patient which comprises administering orally to a patient suffering from uremia a microencapsulated and/or enteric-coated composition.

3 Claims, No Drawings

OTHER PUBLICATIONS

Owadu, A. and Shiigai, T., "Effects of Oral Adsorbent AST–120 Concurrent with a Low–Protein Diet on the Progression of Chronic Renal Failure", *Am. J. Nephrol.* 1996 16:124–127.

Prakash, S. and Chang, T.M.S., "Microencapsulated genetically engineered live *E. coli* DH5 cells administered orally to maintain normal plasma urea level in uremic rats", *Nature Med.* 1996 2:883–887.

Prakash S. and Chang T.M.S., "Preparation and In Vitro Analysis of Microencapsulated Genetically Engineered *E. coli* DH5 Cells for Urea and Ammonia Removal", Biotechnology and Bioengineering 1995 46:621–26.

Setala, K., "Bacterial enzymes in uremia management", *Kidney Intl.* 1978 8:S–194–S–202.

Shimizu et al., "Removal of uremic waste metabolites (chiefly urea) by chemically surface–treated dialdehyde starch", *Chemical Abstracts* 1982 97:222900 3p.

Sparks R.E., "Gastrosorbents in the therapy of uremia: Inferences from intestinal loop dialysis", *Kidney Int.* 1975 Suppl 7:S–373–S–376.

Twiss E.E. and Kolff W.J., "Treatment of Uremia by Perfusion of an Isolated Intestinal Loop", *JAMA* 1951 146:1019–1022.

Yatzidis et al., "Newer oral sorbents in uremia", *Clinical Nephrology* 1979 11:105–106.

Waynforth, H.B. and Flecknell, P.A. Nephrectomy. In: Experimental and surgical techniques in the rat. 2nd ed., 1992, Academic Press (Harcourt, Brace, Jovanovich), London, pp. 29, 274–275.

Wrong O., "Various views on anonymity", *Nature Medicine* 1997 2–3.

* cited by examiner

PREBIOTIC AND PROBIOTIC COMPOSITIONS AND METHODS FOR THEIR USE IN GUT-BASED THERAPIES

FIELD OF THE INVENTION

The invention relates to pharmaceutical compositions and methods of using these compositions to treat renal, hepatic and gastrointestinal diseases by eliminating toxins and other metabolic waste products and reducing or retarding undesirable bacterial over growth. In one embodiment, the pharmaceutical composition comprises a prebiotic, a probiotic, an ammoniaphilic bacteria, and sorbents, all of which are microencapsulated and/or enteric coated. Alternatively, the probiotic, prebiotic and ammoniaphilic bacteria are administered together in a microencapsulated gelatin capsule, while the sorbents, if needed, are administered separately in a microencapsulated and/or enteric coated formulation. These pharmaceutical compositions are useful in treating renal and hepatic diseases and bacterial overgrowth in the gastrointestinal tract.

BACKGROUND OF THE INVENTION

Kidney disease is ranked fourth among the major diseases in the United States afflicting over 20 million Americans. More than 90,000 patients die each year because of kidney diseases. In recent years the number of chronic kidney failure patients has increased about 11 percent annually. About 80,000 Americans on dialysis die of various complications each year and more than 27,000 are on waiting lists for kidney transplants each year with only about 11,000 of these patients receiving transplants. Further, nearly 250,000 Americans suffer from end stage renal disease (ESRD), which is the final stage in chronic renal failure.

In normal, healthy humans, metabolic waste nitrogen is primarily excreted via the kidneys as urea in the urine. However, in individuals with kidney disease, as well as a number of other diseases such as inborn errors in urea cycle enzyme deficit, waste nitrogen accumulates in the body thereby manifesting toxic symptoms. Hyperammonium can lead to mental retardation and, in severe cases, coma.

Currently hemo- or peritoneal-dialysis and renal transplant are the only treatment modalities. However, the economic costs of these treatment modalities are extremely high. For example, in 1996 in the United States alone, the annual cost of ESRD treatment was over 14 billion dollars. In developing and underdeveloped countries with low health care budgets, ESRD patients are deprived access to such treatments due to their high costs. Accordingly, there is a need for alternative modalities of treatment for uremia.

A number of treatment attempts have been based on the use of the bowel as a substitute for kidney function. During a normal digestive process the gastrointestinal tract delivers nutrients and water to the bloodstream and eliminates waste products and undigested materials through the bowel. The intestinal wall regulates absorption of nutrients, electrolytes, water and certain digestive aiding substances such as bile acids. The intestinal wall also acts as a semi-permeable membrane allowing small molecules to pass from the intestinal tract into the bloodstream and preventing larger molecules from entering the circulation.

Nitrogenous wastes such as urea, creatinine and uric acid, along with several other small and medium molecular weight compounds, flow into the small intestine and equilibrate across the small intestine epithelium. Studies of intestinal dialysis have shown a daily flow of 71 grams of urea, 2.9 grams of creatinine, 2.5 grams of uric acid and 2.0 grams of phosphate into the intestinal fluid (Sparks, R. E. Kidney Int. Suppl. 1975 Suppl 3, 7:373–376). Accordingly, various invasive and noninvasive attempts including external gut fistula, intestinal dialysis, induced diarrhea, and administration of oral sorbents and/or encapsulated urease enzyme have been made to extract uremic waste from the gastrointestinal tract (Twiss, E. E. and Kolff, W. J. JAMA 1951 146:1019–1022; Clark et al. Trans. Am. Soc. Artif. Intrn. Organs 1962 8:246–251; Pateras et al. Trans. Am. Soc. Artif. Intrn. Organs 1965 11:292–295; Shimizu et al. Chemical Abstracts 1955 103:129004; Kjellstrand et al. Trans. Am. Soc. Artif. Intern. Organs 198127:24–29; and Kolff, W. J. Kidney Int. 1976 10:S211–S214).

Activated charcoal was the first oral sorbent studied for treatment of uremia. Activated charcoal is a highly porous material with large surface area obtained by carbonization of organic materials such as wood, petroleum, coal, peat, and coconut shell followed by activation with steam, carbon dioxide or chemicals such as zinc chloride. Solute adsorption by activated charcoal depends on a number of factors including concentration of the solute in bulk phase, chemical nature of the solute, temperature, and pH. In general, however, activated charcoal binds more avidly to non-polar solutes than polar solutes. In in vivo studies, 190 grams of activated charcoal was required to remove 450 mg of creatinine (Goldenhersh et al. Kidney Int. 1976 10:8251–8253). This reduced efficacy is believed to be due to adsorption of other lipophilic compounds such as cholesterol and related bile acids (Kolff, W. J. Kidney Int. 1976 10:8211–8214; Goldenhersh et al. Kidney Int. 1976 10:8251–8253). Microencapsulation of activated charcoal has been shown to reduce the amount of charcoal needed to 50 grams (Goldenhersh et al. Kidney Int. 1976 10:8251–8253).

AST-120, a proprietary and specially prepared, coated material of porous carbon of 0.2 to 0.4 mm, has been demonstrated to be a more effective charcoal based adsorbent. A dose of 3.2 to 7.2 grams to uremic patients has been disclosed to delay the rise in serum level of creatinine and delay the onset of renal dysfunction in nephrectomized rats as well as 27 uremic patients (Owadu, A. and Shiigai, T. Am. J. Nephrol. 1996 16(2): 124-7; and Okada, K. and Takahashi, S. Nephrol. Dial. Transplant. 1995 10 (5): 671-6). AST-120 as an oral adsorbent also delays the progression of renal failure (Miyazaki, T. et al. Nephrol Dial Transplant November 2000; 15(11): 1773-81).

Several studies have shown that ingestion of dialdehyde starch, also referred to as oxystarch, results in increased excretion of non-protein nitrogen (Giordano et al. Bull. Soc. Ital. Biol. Sper. 1968 44:2232–2234; Giordano et al. Kidney Int. 1976 10:S266-8268: Friedman et al. Proc. Clin. Dia. Trans. Forum 1977 7:183–184). Unlike activated charcoal where adsorption of the uremic solute is a physical process easily reversible, dialdehyde starch binds urea and ammonia via chemisorption involving covalent binding to the two-aldehyde groups. However, like activated charcoal, ingestion of very large amounts of about 30–50 grams of oxystarch only removed 1.5 grams of urea. Additional studies wherein dialdehyde starch and activated charcoal were both ingested demonstrated some improvement in uremic waste removal (Friedman et al. Proc. Clin. Dia. Trans. Forum 1977 7:183–184). Further, coating of dialdehyde starch with gelatin and albumin resulted in 6-fold better sorbency as compared to uncoated dialdehyde starch (Shimizu et al. Chemical Abstracts 1982 97:222903). More recently, retardation of progression of chronic renal failure has been shown following administration of chitosan coated oxycellulose or cellulose dialdehyde (Nagano al. Medline Abstract UI 96058336 1995).

Locust bean gum, a naturally available carbohydrate based polymeric oral sorbent, when administered at 25 grams/day in cottonseed oil to uremic patients, was also demonstrated to remove significant amounts of urea, creatinine and phosphate. Further, locust bean gum adsorbs about 10 times its own weight in water (Yatzidis et al. Clinical Nephrology 197911:105–106). Dietary supplementation with gum arabic fiber has also been demonstrated to increase fecal nitrogen excretion and lower serum nitrogen concentration in chronic renal failure patients on low protein diets (Bliss et al. Am. J. Clin. Nutr. 1996 63:392-98).

Encapsulated urease enzyme has also been investigated as a non-absorbable oral sorbent for binding ammonia. In early studies zirconium phosphate and encapsulated urease enzyme were used as a non-absorbable oral sorbent for binding ammonia (Kjellstrand et al. Trans. Am. Soc. Artif. Intern. Organs 1981 27:24–29). A liquid-membrane capsule device with encapsulated urease to hydrolyze urea to ammonia and citric acid to neutralize the ammonia has also been investigated (Asher et al. Kidney Int. 1976 10:8254–8258). Soil bacteria have also been used to recycle urea as metabolically useful amino acids (Setala, K. Kidney Intl Suppl. 1978 8:8194-202).

In addition, genetically engineered *E. herbicola* cells have been encapsulated and demonstrated to convert ammonia into usable amino acids for the cells before being eliminated via the bowel. Microencapsulated genetically engineered *E. coli* DH5 cells have also been shown to be effective in removal of urea and ammonia in an in vitro system and in a uremic rat animal model (Prakash, S. and Chang, T. M. S. Biotechnology and Bioengineering 1995 46:621-26; and Prakash, S. and Chang, T. M. S. Nature Med. 19962:883–887). However, administration of genetically engineered bacteria poses regulatory and safety concerns and raises ethical issues which may lead to noncompliance by patients.

For effective treatment of renal failure, moreover, it has been estimated that at least 10 to 25.0 grams of urea, 1.0 to 2.5 grams of creatinine, 0.7 to 1.5 grams of uric acid must be removed. Accordingly, there is a need for more effective treatments, which remove multiple uremic toxins at higher concentrations to alleviate the symptoms of uremia in patients.

Small bowel bacterial overgrowth (SBO) is yet another clinical manifestation of progress kidney failure wherein the glomerular filtration rate falls below 20 ml/minute. There is an intestinal influx of nitrogenous waste. As a result, there is a profound overgrowth of bacteria with concomitant variation in the beneficial bacterial versus those which are pathogenic and are able to produce secondary toxic materials such are carcinogenic and mutagenic compounds such as amines, nitroso amines, phenols and indole derived compounds.

The human gastrointestinal tract harbors a complex microbial ecosystem containing a large number and variety of bacteria. The resident bacterial population in the human gastrointestinal tract has a major impact on gastrointestinal function and thereby on human health and well being. Among these, some bacteria are opportunistic or considered to be detrimental and cause adverse conditions such as diarrhea, infections, gastroenteritis and endotoxaemia, while some bacteria species are considered as "probiotic", in that they perform beneficial functions for the human organism (Holzapfel W H, et al. *Int J Food Microbiol* May 26, 1998; 41(2): 85–101).

Among the probiotic bacteria, Bifidobacteria species are the most prominent. Bifidobacteria species, when in live and viable form, stimulate the immune system and exert a competitive exclusion of pathogenic and putrefactive bacteria, reduce the amounts of ammonia and cholesterol in the blood, and promote absorption of minerals. In addition, Bifidobacteria have been suggested to exert a preventive action against colon cancer, by reducing the activity of some enzymes that convert procarcinogen substances into carcinogen substances (von Wright, et al. *Eur J Gastroenterol Hepatol* November 1999; 11(11): 1195–1198).

The lactic bacteria such as *Lactobacillus bulgaricus, Lactobacillus acidophilus, Lactobacillus casei, Lactobacillus plantarum* and *Streptococcus faecium. Streptococcus thermophilus* are also probiotic. These bacteria produce antagonist effects against pathogenic microorganisms, stimulate the immune system, improve lactose digestion, perform a lypolytic activity making fats more digestible, reduce plasmatic values of cholesterol, protect the intestinal mucosa ensuring an even assimilation of the nutritive substances, produce polysaccharides that are active on some tumors, and reduce viability of some enzyme-producing microorganisms catalyzing conversion of procarcinogen substances into carcinogenic substances.

It is believed that the probiotic bacteria exert their effects in a synergistic manner to curtail and retard the growth of pathogenic/detrimental bacteria of the gut (Marteau, PR et al. Am J Clin Nutr Feb; 73(2 Suppl): 430S–436S; Cummings JH, et al. Am J Clin Nutr February 2001; 73(2 Suppl): 415S–420S).

The intestinal bacteria flora can be reduced, become unbalanced or be eliminated in patients undergoing antibiotic treatment and other therapies, and in individuals suffering from inflammatory intestinal diseases, kidney disease and liver disease. In addition, it has been shown that during normal aging the Bifidobacteria population is reduced while the concentration of pathogenic and putrefactive bacteria concomitantly increases (Orrhage K., et al. Drugs Exp Clin Res 2000; 26(3): 95–111).

It is also known that beneficial effects of microbes such as the Bifidobacterium species are in part due to their ability to ferment nondigestible sugars, known as prebiotics, present in the colon. A prebiotic is a non-digestible food ingredient that beneficially affects the host by selectively stimulating the growth and/or the activity of one or a limited number of bacteria in the colon. Prebiotics are typically thought of as carbohydrates of relatively short chain length. Prebiotics are like other carbohydrates that reach the cecum, such as nonstarch polysaccharides, sugar alcohols, and resistant starch, in being substrates for fermentation. They are, however, distinctive in their selective effect on the microflora. To be effective, prebiotics they must reach the cecum (Bezkorovainy, A. Am J Clin Nutr February 2001; 73(2 Suppl): 399S–405S).

Nondigestible oligosaccharides that seem to exert the best prebiotic effects are inulin-type fructans that are resistant to digestion by gastric acid and pancreatic enzymes in vivo. In pure culture, most species of bifidobacteria are adapted to the utilization of these nondigestible oligosaccharides. However, many other bacteria are also capable of metabolizing them. When inulin and oligofructose or lactulose were added to a controlled diet, significant increases were noted in colonic bifidobacterial populations, and these changes appears to promote both colonic and systemic health through modification of the intestinal microflora. Inulin and oligofructose are rapidly and completely fermented by the colonic microflora with the products of fermentation being acetate and other short-chain fatty acids. The effectiveness of inulin, lactulose and other non absorbable carbohydrates stems from the fact that they are disaccharides or oligosaccharides and that the human gastrointestinal tract lacks the enzyme disaccharidase to hydrolyze them. These fermentable carbohydrates are therefore not digested and enter the colon intact. In the colon, resident flora which possess the enzyme disaccharidase, are able to hydrolyze these oligosaccharides or disaccharides and use them for energy and growth. During this process, they produce large amounts of short chain fatty acids which acidify the intestinal content, and via osmotic mechanism draw water into to the intestinal lumen, provide a laxative effect, prevent over growth and facilitate ammonia and other waste nitrogen product elimination. Like lactulose, they may also result in the growth of the fecal biomass, and in doing so, entrap ammonia for bacterial protein synthesis or conversion to the ammonium ion. Through stimulation of bacterial growth and fermentation, prebiotics also affect bowel habit and are mildly laxative (Jenkins, D J et al. J Nutr July 1999; 129(7 Suppl): 1431S–1433S).

U.S. Pat. No. 5,733,568 teaches the use of microencapsulated Lactobacillus bacteria for treatment of antibiotic associated or other acute and chronic diarrhea as well as for skin and vaginal yeast infections. The microencapsulation is said to prevent inactivation of the bacillus and to deliver it to the intestine as well as to avoid lactose intolerance seen in said diarrheas.

U.S. Pat. No. 5,032,399 teaches the use of species of *Lactobacillus acidophilus* to adhere to intestinal mucosa and thereby reduce gastrointestinal side effects of antibiotic therapy that reduces beneficial bacteria population.

U.S. Pat. No. 5,531,988 teaches, in addition to beneficial bacteria, use of immunoglobulin in the composition as a dietary supplement.

U.S. Pat. No. 5,840,318 also teaches a beneficial bacterial composition that can modulate the immune system of animals.

Use of probiotics such as *Lactobacillus acidophilus* has been suggested to curtail the bacterial overgrowth and the accumulation of uremic toxins and carcinogenic compounds. Unabsorbable carbohydrate in the diet of uremic patients has also been shown to increase fecal nitrogen. Use of lactulose and dietary fiber has also been shown to reduce plasma urea 11 to 27% and increase fecal nitrogen excretion to 39 to 62% (Wrong, O., Nature Medicine 2–3, 1997).

One of the major deficits of these prior art approaches, however, is that they tend to address individual uremic solutes or toxins. However, proper clinical management of renal, hepatic and gastrointestinal diseases or disorders actually requires alleviation of multiple symptoms.

SUMMARY OF THE INVENTION

The object of the present invention is to provide for an integrated, gut-based, low cost alternative treatment for renal insufficiency, liver insufficiency, inborn error of urea metabolism and gastrointestinal disorders and diseases. In the present invention, unlike the prior art, more than one symptom is alleviated at the same time. Further, the beneficial effects of intestinal flora in restoring normal health are harnessed.

Accordingly, the present invention provides pharmaceutical compositions comprising a probiotic to restore normal balance between beneficial bacteria and detrimental bacteria, to remove excess urea-waste product of normal protein metabolism thereby reducing the burden on ailing kidney, and to remove ammonia to avert mental retardation and related conditions. The pharmaceutical compositions of the present invention also comprise a prebiotic to stimulate beneficial bacterial population as well as to ensure viability of the probiotic so that nitrogen sources such as urea and ammonia are effectively utilized. In addition, the pharmaceutical compositions may comprise an ammoniaphilic urea degrading microorganism with high alkaline pH stability and high urease activity. In some embodiments, the probiotic may function to restore normal balance between beneficial bacteria and detrimental bacteria, to remove excess urea-waste product of normal protein metabolism thereby reducing the burden on ailing kidney, and to remove ammonia to avert mental retardation and related conditions, as well as to act as the ammoniaphilic urea degrading microorganism.

In one embodiment, pharmaceutical compositions of the present invention may further comprise a water sorbent to remove water in diarrhea and renal insufficiency, a mixture of adsorbents to remove other nitrogen metabolic wastes and bacterial over growth products such as uric acid, creatinine and guanidines, and phenols and indoles, and/or an inorganic phosphate adsorbent to maintain phosphate balance. In a preferred embodiment, activated charcoal and inorganic phosphate adsorbent are combined together in the composition for synergistic effect and to reduce the relative proportion of these two components in relation to the probiotic and prebiotic. Further, since the probiotic and prebiotic remove most of the urea and curtail bacterial overgrowth so that the amount of other normal nitrogen waste products and bacterial end products are minimized minimal, less activated charcoal and inorganic adsorbents are required as compared to prior art compositions.

Alternatively, pharmaceutical compositions comprising a probiotic, prebiotic and ammoniaphilic microorganism can be used prophylactically in patients with acute or chronic symptoms of uremia due progression of the disease and the water sorbent, a mixture of adsorbents and/or an inorganic phosphate adsorbent may be administered separately only when necessary to control for diarrhea and other gastrointestinal disorders.

Pharmaceutical compositions of the present invention are preferably enteric coated or microencapsulated for delivery to the ileal or colonic regions of the bowel of a patient in need thereof.

The pharmaceutical compositions are particularly useful for preventing or delaying the need for dialysis in kidney patients and to reduce the frequency and/or duration of dialysis.

DETAILED DESCRIPTION OF THE INVENTION

In kidney failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Uremic toxins can be defined as solutes that: (I) are normally excreted by healthy kidneys, (ii) accumulate progressively during the development of renal failure so that their concentration increases, and (iii) inhibit various physiologic and biochemical functions; as a whole, they contribute to a complex set of clinical symptoms that comprise the Uremic Syndrome. Examples of uremic toxins include, but are not limited to, ammonia, urea, creatinine, phenols, indoles, and middle molecular weight molecules. More specifically, in uremia, the concentration of serum creatinine, blood urea nitrogen (BUN), uric acid, and guanidino compounds such as N-methyl guanidine (NMG) and guanidino succinic acid, (GSA) are significantly altered with accompanying abnormalities in acid-base equilibrium, electrolytes and water retention. In addition there are several known and unknown substances of low and middle molecular weight which have been identified as uremic toxins which also accumulate. If untreated the acidosis and uremia can cause coma and eventually death.

Further, as a result of poor clearance of waste products of metabolism, there are some compensatory as well as adaptive processes, which further complicate the condition. For example, bacterial overgrowth of the normal flora of the gut occurs when kidney function is reduced to less than 20% and creatinine levels in the serum increase to 8 mg/dl. Substantially increased metabolism of normal substrates and a large variety of toxic amines, such as methylamine, dimethylamine, trimethylamine, phenols and indole metabolites also occur from this bacterial outgrowth. When the small gut bacterial growth increases, there is an increase in ammonia release, which then enters the enterohepatic circulation and is converted to urea.

The introduction of renal dialysis has contributed to rapid progress in the clinical treatment of renal failure and elucidation of uremia. When a patient has mild kidney failure where the serum creatinine level is less than 400 $\mu$mol/L, the patient does not require renal replacement therapy such as dialysis or renal transplant. However, in general, when the serum creatinine level rises to 900 $\mu$mol/L, the patient needs routine dialysis or a kidney transplant to survive.

Dialysis can serve as a lifetime therapy for ESRD patients. Phosphate binders such as calcium acetate, calcium carbonate or aluminum hydroxide are generally prescribed for uremic patients receiving dialysis to reduce elevated phosphate levels. In general, however, dialysis is very expensive, inconvenient, time consuming and may occasionally produce one or more side effects. With a successful kidney transplant, a patient can live a more normal life with less long-term expense. However, there are also high costs associated with transplant surgery, the recovery period and the continuous need for antirejection medications. Further, there are often times a shortage of suitable donors. Accordingly there is a need for alternative strategies.

The present invention relates to pharmaceutical compositions comprising a mixture of probiotics, prebiotics, and ammoniaphilic bacteria with high urease activity, and/or sorbents with specific adsorption affinities for uremic toxins such as creatinine, uric acid, phenols, indoles, middle molecular weight molecules and inorganic phosphate along with a water sorbent, for use in the alleviation of uremia. In a preferred embodiment, the composition comprises a probiotic bacteria, a prebiotic such as inulin, a fructan oligosaccharide, lactulose and other vegetable fibers, an ammoniaphilic urea degrading microorganism with high alkaline pH stability and high urease activity, and adsorbents such as locust bean gum with a specific adsorption affinity for creatinine and urea, activated charcoal with a specific adsorption affinity for creatinine, guanidines, phenol, indican and middle molecular weight undefined components, and water absorbents such as psillium fiber, guar gum and locust bean gum.

It is preferred that the bacterial source for the probiotic be capable or metabolizing urea and ammonia, preferably to amino acids which can be used by the bacteria or the patient. Exemplary bacterial species with these capabilities are Bifidium bacteria species and Lactobacillus species.

*Bacillus pasteurii* and *Sporosarcina ureae* are closely related soil bacteria, both of which have high avidity for urea. These bacteria are non-pathogenic and safe. Further, they grow well in high concentrations of ammonium ion and alkaline pH, which are present in the intestine, particularly in uremic conditions. In *Bacillus pasteurii* and *Sporosarcina ureae*, no accumulation of ammonium occur and these organisms depend on passive diffusion of ammonia across the cell membrane. Both *B. pasteurii* and *S. ureae* exhibit low affinities for ammonium, with Km values of 55.2 mM and 36.7 mM respectively. In contrast to *P. vulgaris*, a pathogen which can only grow in neutral pH and low ammonium concentration of 2 mM, *B. pasteurii* and *S. ureae* require high concentrations of ammonium (40 mM) and alkaline pH (Kaltwasser, Morsdorf G. H. Arch Microbiol 1989; 152(2): 125-31). In addition, it is known that urease of *Sporosarcina ureae* has a specific activity of greater than 9300 $\mu$mol of urea degradation per minute at a pH of 7.5.

Accordingly, examples of preferred bacterial sources useful as ammoniaphilic bacteria in the present invention include, but are not limited to, *Sporosarcina ureae, Bacillus pasteurii*, trained lactobacillus and Bacillus species and a novel Lactobacillus KB-I or other suitable Bacillus species.

In some embodiments, the probiotic may function to restore normal balance between beneficial bacteria and detrimental bacteria, to remove excess urea-waste product of normal protein metabolism thereby reducing the burden on ailing kidney, and to remove ammonia to avert mental retardation and related conditions, as well as to act as the ammoniaphilic urea degrading microorganism. Thus, in this embodiment, a separate ammoniaphilic urea degrading organism may not be required. Instead, in this embodiment, the probiotic and the ammoniaphilic urea degrading organism comprise the same species of bacteria.

Compositions comprising these mixtures are enteric coated and/or microencapsulated. Enteric coating of the composition is specifically designed to deliver the sorbents and bacterial source at the ileal and colonic regions of the bowel where maximal resorption of uremic solutes and other molecules are found to occur. This is preferably achieved via an enteric coating material that disintegrates and dissolves at a pH of 7.5 or higher. Examples of enteric coatings with these characteristics include, but are not limited to, Zein, polyglycolactic acid, polylactic acid, polylactide-coglycolide and similar coating materials. Enteric coatings also enable delivery of the sorbents to their site of action in relatively native form without binding of various digestive materials to the sorbents prior to reaching the target region.

Alternatively, compositions of the present invention are microencapsulated, thus permitting the compositions to perform like microscopic dialysis units as described by Chang, T. M. S. (Artificial Cells, Chapter 5, in Biomedical Applications of Microencapsulation, edited by Lim, F. CRC Press Florida, pp 86–100). In this embodiment, the composition is coated with a non-absorbable polymeric compound which permits only small and middle-sized molecules into the core wherein the mixture of solvent and bacterial source are located. Examples of non-absorbable polymeric coatings for microencapsulation include, but are not limited to, alginate/alginic acid, chitosan, cellulose acetate phthalate, hydroxyethyl cellulose and similar coating materials. Microencapsulation prevents the binding of macromolecules and other digestive materials which substantially reduce the efficacy of the sorbents to specifically adsorb the uremic solutes to the sorbents of the mixture. The microcapsules pass through the bowel, with the mixture of sorbents adsorbing multiple uremic solutes and the bacterial source metabolizing urea and ammonia and urea, and are then excreted intact from the bowel. Thus, in this embodiment, the patient is protected from the possibility of microbial infection by the bacterial source as the bacterial source is kept within the microcapsule.

In a preferred embodiment of the present invention, the pharmaceutical compositions are both microencapsulated and enteric coated.

Pharmaceutical compositions of the present invention may further comprise a phosphate binding agent such as aluminum hydroxide gel, calcium carbonate or calcium acetate, magnesium hydroxide gel and/or a water binding agent such as psyllium fibers, naturally occurring gums such as locust bean gum, guar gum or modified starches.

Pharmaceutical compositions of the present invention are administered orally to subjects in need thereof to decrease the build-up of toxins and metabolic wastes and/or to inhibit or decrease the over growth of undesirable bacteria in the subject. In one embodiment, the pharmaceutical composition is administered to a subject with uremia to alleviate the symptoms of uremia. By "alleviation of symptoms" of uremia, it is meant that the composition removes sufficient levels of uremic toxins such that a patient suffering from uremia either does not require dialysis, requires dialysis less frequently or for shorter durations, or does not require initiation of dialysis as soon. Compositions of the present invention can also be administered to a subject in need thereof to treat not only renal insufficiency and inborn error of urea metabolism, but also liver insufficiency and gastrointestinal disorders and diseases.

In a preferred embodiment, oral delivery of the composition is accomplished via a 2 to 4 ounce emulsion or paste mixed with an easy to eat food such as a milk shake or yogurt. The microencapsulated bacterial probiotic and prebiotic can be administered along with the mixture of sorbents in the emulsion or paste or separately in a swallowable gelatin capsule.

A mathematical model of solute transport of oral sorbents has been developed based on the diffusion controlled solute flux into the intestinal lumen followed by physical binding or chemical trapping (Gotch et al. Journal of Dialysis 1976–1977 1(2): 105–144). This model provides the theoretical basis of solute removal through the gut.

For example, gut clearance of urea is 10 to 12 ml/minute in normal renal function and is reduced to 3 to 4 ml/minute in patients with severely reduced renal function. This reduction in the clearance rate is independent of blood urea concentration and directly related to impaired renal function. The normal creatinine clearance rate is 2 to 5 ml/minute.

Further, at steady state, as rate of mass generation is equal to rate of mass elimination, the first order sorbent promoted gut clearance of any solute is given by the mass balance equation:

$$Gs = (Kr + Kg)Cs,$$

where $Gs$=rate of solute generated, $Kr$=rate of renal clearance, $Kg$=rate of gut clearance and $Cs$=concentration of solute.

The process of sorbent binding, for a given amount of sorbent, is saturable. Thus, below the saturation levels, as the rate of gut clearance of the solute is first order, the above equation can be depicted as:

$$Cs = Gs/(Kr + Kg).$$

Above the saturation levels, as the rate of gut clearance is zero, the equation can be rewritten as:

$$Cs = (Gs - \text{sorbent capacity})/Kr.$$

These equations are useful in predicting the efficacy of solute removal from the gut based in vitro studies.

In fact, this model was applied to Friedman's data on urea elimination by the gut in uremic patients using oxystarch oral sorbent (Friedman et al. Trans. Am. Soc. Artif. Intern. Organs 1974 20:161–167). With these data, the model showed that maximum sorbent capacity for native oxystarch oral sorbent was 1.5 g/day, which is insufficient to replace dialysis or reduce the frequency of dialysis. This model also predicted that for the same patient data, at a protein catabolic rate of 0.95 grams/kg/24 hours and a urea generation of 5 mg/minute, the maximum sorbent capacity of oxystarch should be 7.2 grams of urea nitrogen/day and the gut clearance rate should be 5.6 ml/minute. Sorbent capacity lower than this, such as 5.4 grams of urea/day will at best delay dialysis by months provided the protein catabolic rate can be held at 0.6 grams/kg/24 hours. Thus, this model is useful in determining optimal results for various formulations of compositions of the present invention to alleviate symptoms of uremia in patients.

The following non-limiting examples are provided to further illustrate the present invention.

EXAMPLES

Example 1

Source of Sorbents

Oxystarch (dialdehyde starch) was purchased from MPD-Labs, Feasterville, Pa. This is a pharmaceutical grade material (98% pure) with a moisture content of 13% and possessing a minimum 90% oxidized material as per the certificate of analysis by the supplier.

Locust bean gum (minimum 99% pure) was purchased from. Sigma-Aldrich, St. Louis, Mo.

Activated charcoal, Supra A, pharmaceutical grade (99.9% purity) was purchased from Norit Corporation of America, Atlanta, Ga. Each sorbent material was enteric coated with Zein; microencapsulated with ethocel; and microencapsulated with ethocel and then enteric coated with Zein as the shell materials. Encapsulation runs were performed using a disk process. Three separate shell material solutions were prepared: ethocel alone, Zein alone, and Zein in combination with ethocel. After the shell materials were prepared, each sorbent was added to the shell solution (to provide 60% theoretical payload) and mixed to form a dispersion. The dispersion was then sonicated and pumped at approximately 50 grams/minute onto a disk rotating at approximately 20,000 RPM to create microspheres. The microspheres were formed in a heated cone with an inside temperature of approximately 50° C. to evaporate the ethanol and water. The capsules were collected via a cyclone. The native particle size and the particle size after various encapsulations of these sorbents are depicted in Table 1.

TABLE 1

OXYSTARCH

| Percent Oxystarch | Urea/Creatinine/Uric Acid | Percent Bacteria |
|---|---|---|
| 0.1 | 150/30/30 | 10 |
| 0.2 | 150/30/30 | 10 |
| 0.3 | 150/30/30 | 10 |
| 0.4 | 150/30/30 | 10 |
| 0.5 | 150/30/30 | 10 |

Locust Bean Gum

| Percent LB Gum | Urea/Creatine/Uric Acid | Percent Bacteria |
|---|---|---|
| 0.1 | 150/30/30 | 10 |
| 0.2 | 150/30/30 | 10 |
| 0.3 | 150/30/30 | 10 |
| 0.4 | 150/30/30 | 10 |
| 0.5 | 150/30/30 | 10 |

WATERLOCK ™ (A-220)

| Percent WL | Urea/Creatine/Uric Acid | Percent Bacteria |
|---|---|---|
| 0.1 | 150/30/30 | 10 |
| 0.2 | 150/30/30 | 10 |
| 0.3 | 150/30/30 | 10 |
| 0.4 | 150/30/30 | 10 |
| 0.5 | 150/30/30 | 10 |

Activated Charcoal

| Percent Charcoal | Urea/Creatine/Uric Acid | Percent Bacteria |
|---|---|---|
| 0.1 | 150/30/30 | 10 |
| 0.2 | 150/30/30 | 10 |
| 0.3 | 150/30/30 | 10 |
| 0.4 | 150/30/30 | 10 |
| 0.5 | 150/30/30 | 10 |

Individual Microbes

| Urea/Creatinine/Uric Acid | Percent Inoculation |
|---|---|
| 100/15/15 | 3 |
| 100/15/15 | 5 |
| 100/15/15 | 10 |
| 150/30/30 | 5 |
| 150/30/30 | 10 |

Scanning electron micrographs (SEMS) of the raw materials including dialdehyde starch, locust bean gum, activated charcoal and aluminum hydroxide and the twelve microencapsulation formulations were also prepared. Run 11 produced rod-like capsules which was caused by the material not being fed directly into the center of the disk or by the solids content being too high. Run 11 was repeated as run 13 with the Zein decreased from 15% to 12% and was successful.

In addition to the SEMs of each run, digital photomicrographs were also taken.

Example 2
E. coli DHS and Other Bacterial Sources

Genetically engineered *E. coli* DH5 cells were seeded cultured, grown, harvested and microencapsulated in accordance with procedures described by Chang and Prakash (*Biotechnology and Bioengineering* 1995 46:621–26). Probiotics and ammoniaphilic bacteria of the present invention were treated in the same manner.

Example 3
Formulations

Various probiotics, prebiotics and sorbents were mixed with various food additives to form different formulations of the present invention. Their general components are depicts in the following Table 2.

TABLE 2

| Component | Range (grams) | Most preferred amount (grams) |
|---|---|---|
| Probiotic Bacteria | 5–20 | 12.5 |
| Locust Bean Gum | 10–20 | 15 |
| WATERLOCK ™ | 1–5 | 3 |
| Activated Charcoal | 0.5–2 | 1 |
| inulin | 1–-0 | 5 |
| Food Additives | ~3–~42 | 23 |
| Total | 60 grams | 60 grams |

Component and amount in a 60 g dose (based on B.I.D. intake)

Example 4
In vitro Efficacy Evaluations

A simulated gastric fluid composed of NaCl, HCl and pepsin in distilled water and adjusted to pH 1.2 is prepared according to U.S. Pharmacopoeia procedures for stability testing of formulations under acidic pH and gastric conditions. Every modified sorbent material, and binary and ternary formulation is tested by stirring a quantity of approximately 5 grams into a test solution of simulated gastric juice at 37° C. for 1 to 2 hours to ascertain the integrity of the modified sorbent.

A simulated synthetic intestinal fluid, composed of monobasic potassium hydrogen phosphate, sodium hydroxide, pancreatin mix and distilled water, is also prepared and adjusted to pH 7.5 according to the test solution preparations in U.S. Pharmacopoeia. The intestinal fluid is fortified with uremic solutes to make a solution of 150 milligrams of urea, 30 milligrams of creatinine, and 30 milligrams of uric acid per 100 milliliters of synthetic intestinal fluid.

To vary the concentrations, this stock solution is diluted with non-fortified intestinal stock solution to make 75% and 50% concentrations of variable uremic intestinal fluid solutions. Initially 100%, 75% and 50% concentration uremic intestinal fluid solutions are evaluated with a 15-gram sorbent formulation containing 5 grams each of oxystarch, locust bean gum and activated charcoal. From these data, various experimental parameters including, but not limited to volume, concentration of uremic intestinal fluid, and time of pre- and post-treatment can be optimized. Optimal parameters are then used for all additional sorbent evaluations, formulations and experimental determinations. All experimental observations are made in triplicate.

However, initially, sorbent/formulation test runs of 5, 10 or 15 grams of sorbent or formulation are treated with 500 ml of fortified intestinal fluid of different concentrations in a graduated measuring cylinder and gently shaken for 8 hours. Samples are drawn from the supernatant at one-hour intervals, centrifuged if necessary, and analyzed for urea creatinine and uric acid via commercially available kits (Sigma Diagnostics Company, St. Louis, Mo.). Once the adsorption capacity and equilibration times are determined, this period, estimated to be at least 2 hours, will be used.

*Lactobacillus sporogenes, L. acidophilus, Bacillus Pasteurii* (B.p.) and *Escherichia coli* DH5 (E.c.) are evaluated for their ability to eliminate urea from fortified artificial intestinal fluid (FAIF: 100/150 mg/dL urea, 15/30 mg/dL creatinine and 15/30 mg/dL uric acid in aqueous pancreatin, $KH_2PO_4$ and NaOH) via the enzymatic activity of urease. *Bacillus Pasteurii* and *Escherichia coli* DH5 are assessed both in the native state and as alginate-poly-L-lysine-alginate microcapsules. Activated charcoal is added to the FAIF system for the removal of creatinine and uric acid. Locust bean gum is evaluated for its uric acid and creatinine sorbent capacity.

Under sterile conditions, each native bacterium, activated charcoal and locust bean gum are added individually and, in various mixtures, to 50 mL FAIF and incubated at 37° C. and 100 rpm. In a separate study, approximately one millimeter diameter alginate-poly-L-lysine-alginate microcapsules containing B.p. or E.c. are added in quantities that attempt to normalize the protein content of the cells to 50 mL FAIF. Aliquots are taken at 1, 2, 3, 4, 6 and 24 hours and evaluated for the reduction in urea nitrogen, the formation of ammonia and the stability of uric acid and creatinine. All assays are performed in triplicate and the results taken as the average.

After the bacterial concentration has been optimized, Water Lock® (WL) A-220 is added in varying concentrations to solutions of 50 mg/dL ammonia and evaluated for ammonia uptake. Analytical determinations of the ammonia concentration are determined from the supernate of filtered suspension. Locust Bean Gum (LBG) is then added to the system in varying concentrations to high concentrate FAIF only without the addition of bacteria. The system is analyzed for residual creatinine and uric acid after 2 hours incubation at 37° C. and 100 rpm. Once an appropriate concentration of LBG is determined, activated charcoal is added in varying amounts to high concentrate FAIF only without the addition of bacteria. The system is incubated at 37° C. and 100 rpm and the residual creatinine and uric acid are determined after 2 hours incubation.

The methods for urea, ammonia, creatinine and uric acid quantitative analysis are commercially available diagnostic kits (Sigma, St. Louis, Mo. Cat Nos. 535 and 171, respectively and Advanced Diagnostics, Inc. Division of Inamco Group, South Plainfield, N.J. Cat Nos. 131 500 and CASO-50, respectively).

Example 5
TNO Gastro-Intestinal Model (TIM)

The TNO gastrointestinal model (TIM) simulates very closely the successful dynamic conditions in the lumen of the gastrointestinal track (van der Werf, et al. J. Agric. Food Chem. 49, 378–383, 2001). Dynamic parameters that are simulated include: food and drink intake; the pH curves and the concentrations of enzymes and proenzymes in the stomach including saliva and small intestines including pancreatic juices; the concentration of bile in different parts of the gut; the kinetics passage of chyme through the stomach and small intestines; and the adsorption of water soluble digestive products and water. In the large intestinal model a complex high density microflora of human origin ferments the undigested food compounds in a natural colonic environment simulating pH values, absorption of water, and absorption of microbial metabolites such as short chain fatty acids and gas. Accordingly, this model is used to evaluate the fate of various formulations of compositions of the present invention in both the small and large intestines.

Example 6
In vivo Studies

Rats weighing approximately 150±15 grams, with a degree of chronic renal failure (CRF) similar to that found in humans with end-stage renal disease approaching the 10 initiation of dialysis are used to test the effects of orally administered microencapsulated sorbents and *E. coli* DH5 cells at removing uremic toxins that accumulate in CRF and in reducing uremic symptoms. Overall, there are 4 groups including a control group, a group with chronic renal failure (n=15) and 2 groups with acute renal failure. Specifically, male rats weighing 250–300 grams, approximately 8 weeks in age, are purchased from Charles River or Harlan and housed in cages which prohibit rats from any access to their feces. Baseline measurements of standard clinical chemistries as well as 20 measurements of compounds considered to be uremic toxins are determined for all animals. Rats are then made either acutely uremic or chronically uremic by surgical procedures.

Acute renal failure is produced by bilateral nephrectomy in accordance with procedures described by Waynforth, H. B. and Flecknell, P. A. Nephrectomy. In: Experimental and surgical techniques in the rat. 2nd ed., 1992, Academic Press (Harcourt, Brace, Jovanovich), London, pp. 29, 274–275. After surgery, rats are randomly paired into age or size matched groups and pair fed. Rats are fed by intragastric administration by a curved dosing needle. One group is treated with oral feeding of sorbents along with Kayexylate to control potassium (treated group). The other group receives Kayexylate alone for potassium control only (control group). Both groups are closely monitored for at least 7 to 10 days. Effective sorbents will result in prolongation of life as compared to the non-treated group.

Chronic renal failure (CRF) is produced by a 2-stage surgical procedure similar to that of the 5/6 nephrectomy model disclosed by Niwa et al. (Miner. Electr. Metab. 1997 23:179–184) and Einbacher and Carter (J. Exp. Med. 1966 123:239–250) but with some modifications found to give a more profound degree of renal failure similar to people closely approaching the need for hemodialysis. In this modified procedure, a soft plastic box is sutured around the remnant kidney to prevent excessive hypertrophy following contralateral nephrectomy. This also aids in controlling organ bleeding.

Specifically, a 2-stage approach is used. On the day of the proposed surgery, food is withheld for one hour. The animal is then anesthetized with the inhalation agent, isoflurane (FORANE). The anesthetized rat is placed on its ventral side, left to right of the surgeon. Both flanks are minimally cleaned of fur with an Oster shaver and prepped with Betadine. A sterile field is prepared on the rat's left flank. A dorsoventral incision is made into the abdomen cavity, down the side of the rat near to the costal border of the thorax on the left side. The left kidney is freed of connective tissue and is pulled out gently, preferably by grasping the perirenal fat. The adrenal gland, which is attached loosely to the anterior pole of the kidney by connective tissue and fat, is gently freed by tearing the attachments. The kidney is positioned to have both poles ligated close to the point where the renal artery enters the organ. A loose lasso of new 4.0 monofilament silk is placed around the upper pole and tied tightly taking care not to break the knot. A double reef knot is used. The organ is examined for excessive bleeding. If necessary, diathermy is used to stop oozing and oxycel is used on the cortex. The same procedure is repeated on the lower pole. The remnant kidney is encased in a pre-made plastic, preferably SARAN wrap, box and secured. The organ is then placed back into the abdomen and the incision closed in 2 layers. The area is swabbed with Betadine and the animal allowed to recover. An analgesic, buprenorphine (0.25 mg/kg) is administered to relive pain. About 3 to 4 weeks later the right kidney is removed. In this surgery, an abdominal approach is used to permit examination of the remnant kidney. The anesthesia is the same, but a midline incision is made along the linea alba, minimizing bleeding. The bowel is gently moved and the left remnant kidney observed to insure some function. Adjustments to the box are made if necessary. Assuming all is well with the left kidney, the right kidney is exposed and freed from its capsule (leaving the adrenal) and then removed by placing a ligature around the renal blood vessels. Another ligature is placed around the ureter as far from the kidney as possible, towards the midline, but without damaging or occluding any collateral blood vessels that may be encountered. The ligature is tied securely with a double reef knot, and the blood vessels are transected next to the kidney, which is then removed. The incision is closed, an analgesic is given and the animal is permitted to recover in a warm area.

Serum creatinine levels of 2.6±0.2 (range 2.3 to 3.5) and blood urea levels of 98±5 with low morbidity (less than 20% by 4 weeks post-op) have been attained consistently in rats with this modified procedure.

Approximately 5 days after the second surgery, contralateral blood is drawn and rats are matched as closely, as possible for weight, serum creatinine and blood urea. They are randomly assigned into a series of 4 groups. Groups A and B are pair fed. Group A consists of CRF rats without any test sorbents. Group B rats receive sorbent. A third group, Group C, is given sorbents and allowed free access to food and water. A comparison between Groups B and C shows the effects of uremia on appetite and nutrition. A fourth, sham operated group, Group D is used as controls. Rats are observed over a 4 to 7 month period during which they have biweekly blood and urine collected and assayed for dimethyl- and/or trimethyl-amine via gas chromatography as described by Dunn et al. Analytical Chemistry 1976 48:41–44. Animals are also weighed weekly and blood pressure and urine osmalities are measured monthly. They are assessed daily for appetite by following food and water intake. Timed urine collections are also performed monthly and spot urine collected biweekly. Skinfold thickness is also assessed as an additional nutritional measurement. Rats are sacrificed at 7 months and terminal bloods are drawn for clinical chemistries as well as other specific tests. Blood, urine and brain tissue are also assayed for dimethylamine. For these studies, sorbents are in a suspension form in sterile saline and are administered orally to the rats using a 12-gauge gastric lavage tube.

What is claimed is:

1. A pharmaceutical composition to alleviate the symptoms of uremia comprising a composition of a probiotic, a prebiotic, a sorbent for inorganic phosphate, an adsorbent for specific uremic solutes other then urea and ammoniaphilic urea degrading microorganism with high alkaline pH stability and high urease activity, said composition being microencapsulated or enteric coated with a material designed to deliver the probiotic, the prebiotic, and ammoniaphilic urea degrading microorganism to their site of action without binding of digestive materials to the composition prior to reaching the target region, wherein said prebiotic ensures the viability of the probiotic, and wherein said microencapsulated or enteric coating prevents the release of the ammoniaphilic urea degrading microorganism into the patient.

2. The pharmaceutical composition of claim 1 wherein the inorganic phosphate adsorbent is selected from aluminum hydroxide gel, calcium hydroxide gel and magnesium hydroxide gel and the specific uremic solute adsorbent is activated charcoal.

3. A pharmaceutical composition to alleviate the symptoms of uremia comprising a composition of a probiotic, a prebiotic, an ammoniaphilic urea degrading microorganism with high alkaline pH stability and high urease activity, a water absorbent, a sorbent for inorganic phosphate and an adsorbent for specific uremic solutes other than urea, said composition being microencapsulated or enteric coated with a material designed to deliver the probiotic, the prebiotic, and ammoniaphilic urea degrading microorganism to their site of action without binding of digestive materials to the composition prior to reaching the target region, and wherein said microencapsulated or enteric coating prevents the infection of a patient from the ammoniaphilic urea degrading microorganism.

* * * * *